US00PP28130P2

(12) United States Plant Patent
Geibel

(10) Patent No.: US PP28,130 P2
(45) Date of Patent: Jun. 20, 2017

(54) ***PELARGONIUM* PLANT NAMED 'CAMPEACL'**

(50) Latin Name: *Pelargonium grandiflorum*
Varietal Denomination: Campeacl

(71) Applicant: ELSNER pac JUNGPFLANZEN GbR, Dresden (DE)

(72) Inventor: Martin Geibel, Dresden (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 0 days.

(21) Appl. No.: 14/998,598

(22) Filed: Jan. 23, 2016

(51) Int. Cl.
*A01H 5/02* (2006.01)

(52) U.S. Cl.
USPC ..... Plt./331

(58) Field of Classification Search
USPC ..... Plt./331
CPC ..... A01H 5/0277
See application file for complete search history.

*Primary Examiner* — Kent L Bell
(74) *Attorney, Agent, or Firm* — C. A. Whealy

(57) ABSTRACT

A new and distinct cultivar of Regal Geranium plant named 'Campeacl', characterized by its upright, outwardly spreading and uniformly mounded plant habit; vigorous growth habit; freely basal branching habit; early and freely flowering habit; red and light pink bi-colored flowers; and no requirement for a cooling treatment for flower initiation and development.

1 Drawing Sheet

Botanical designation: *Pelargonium grandiflorum.*
Cultivar denomination: 'CAMPEACL'.

BACKGROUND OF THE INVENTION

The present invention relates to a new and distinct cultivar of Regal Geranium plant, botanically known as *Pelargonium grandiflorum*, and hereinafter referred to by the name 'Campeacl'.

The new Regal Geranium plant is a product of a planned breeding program conducted by the Inventor in Dresden, Germany. The objective of the breeding program is to develop new early flowering Regal Geranium plants that do not require a cooling treatment for flower development and have good summer performance.

The new Regal Geranium plant originated from a cross-pollination made by the Inventor in Dresden, Germany during the summer of 2011 of two unnamed proprietary selections of *Pelargonium grandiflorum*, not patented. The new Regal Geranium plant was discovered and selected by the Inventor as a flowering plant from within the progeny of the stated cross-pollination in a controlled greenhouse environment in Dresden, Germany during the spring of 2012.

Asexual reproduction of the new Regal Geranium plant by vegetative terminal cuttings in a controlled greenhouse environment in Dresden, Germany since October, 2012 has shown that the unique features of this new Regal Geranium plant are stable and reproduced true to type in successive generations.

SUMMARY OF THE INVENTION

Plants of the new Regal Geranium have not been observed under all possible combinations of environmental conditions and cultural practices. The phenotype may vary somewhat with various environmental conditions such as temperature and light intensity without, however, any variance in genotype.

The following traits have been repeatedly observed and are determined to be the unique characteristics of 'Campeacl'. These characteristics in combination distinguish 'Campeacl' as a new and distinct Regal Geranium plant:

1. Upright, outwardly spreading and uniformly mounded plant habit.
2. Vigorous growth habit.
3. Freely basal branching habit.
4. Early and freely flowering habit.
5. Red and light pink bi-colored flowers.
6. No required cooling treatment for flower development.

Plants of the new Regal Geranium differ primarily from plants of the parent selections in flower color. In addition, plants of the new Regal Geranium are more uniform than plants of the parent selections.

Plants of the new Regal Geranium can also be compared to plants of the *Pelargonium grandiflorum* 'Regpin', disclosed in U.S. Plant Pat. No. 26,257. In side-by-side comparisons conducted in Dresden, Germany, plants of the new Regal Geranium differ from plants of 'Regpin' in the following characteristics:

1. Plants of the new Regal Geranium are broader than and not as upright as plants of 'Regpin'.
2. Plants of the new Regal Geranium have smaller leaves than plants of 'Regpin'.
3. Plants of the new Regal Geranium have smaller inflorescences and flowers than plants of 'Regpin'.
4. Plants of the new Regal Geranium and 'Regpin' differ in flower color as plants of 'Regpin' have pink and dark purple bi-colored flowers.
5. Plants of the new Regal Geranium have shorter peduncles and pedicels than plants of 'Regpin'.

BRIEF DESCRIPTION OF THE PHOTOGRAPH

The accompanying colored photograph illustrates the overall appearance of the new Regal Geranium plant showing the colors as true as it is reasonably possible to obtain in colored reproductions of this type. Colors in the photograph may differ slightly from the color values cited in the detailed botanical description which accurately describe the colors of the new Regal Geranium plant.

The photograph comprises a side perspective view of a typical flowering plant of 'Campeacl' grown in a container.

DETAILED BOTANICAL DESCRIPTION

The aforementioned photograph and following observations, measurements and values describe plants grown during the winter, spring and summer in 19-cm containers in a glass-covered greenhouse in Dresden, Germany and under cultural practices typical of commercial Regal Geranium production. During the production of the plants, day temperatures averaged 18° C., night temperatures averaged 16° C. and light levels ranged from 15 kilolux to 100 kilolux. Plants were five months old when the photograph was taken and nine months old when the description was taken. In the detailed description, color references are made to The Royal Horticultural Society Colour Chart, 1995 Edition, except where general terms of ordinary dictionary significance are used.

Botanical classification: *Pelargonium grandiflorum* 'Campeacl'.

Parentage:

*Female, or seed, parent*.—Unnamed proprietary selection of *Pelargonium grandiflorum*, not patented.

*Male or pollen parent*.—Unnamed proprietary selection of *Pelargonium grandiflorum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer and winter*.—About four weeks at temperatures about 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright, outwardly spreading and uniformly mounded plant habit; inverted triangle; densely foliated; vigorous growth habit; freely basal branching habit with numerous lateral branches developing per plant.

*Plant height, to top of umbels*.—About 33 cm.

*Plant height, to top of leaves*.—About 27 cm.

*Plant width*.—About 55 cm.

*Lateral branches*.—Length: About 16 cm. Diameter: About 5 mm. Internode length: About 2 cm. Texture: Moderately pubescent. Color: Close to 144A.

Leaf description:

*Arrangement*.—Alternate or opposite; simple.

*Length*.—About 3 cm.

*Width*.—About 3.5 cm.

*Shape*.—Cordate; palmately lobed.

*Apex*.—Acute.

*Base*.—Cordate, open.

*Margin*.—Serrate.

*Venation pattern*.—Palmate.

*Texture, upper surface*.—Smooth, glabrous; leathery, rough.

*Texture, lower surface*.—Sparsely pubescent along veins; leathery, rough.

*Color*.—Developing and fully expanded leaves, upper surface: Close to 137B; venation, close to 137B. Developing and fully expanded leaves, lower surface: Close to 146B; venation, close to 146B. Zonation pattern: None discernible.

*Petioles*.—Length: About 3 cm. Diameter: About 1.5 mm. Texture, upper and lower surfaces: Slightly pubescent. Color, upper and lower surfaces: Close to 146B.

Flower description:

*Flower arrangement and flowering habit*.—Single rotate flowers arranged in inversely conical umbels arising from apical leaf axils; umbels displayed above the foliar plane on strong peduncles; flowers face upright to outwardly; freely flowering habit; about three to four flowers per umbel and numerous umbels in flower at the same time.

*Fragrance*.—None detected.

*Flowering season*.—Early flowering habit, plants begin flowering about five months after planting; in outdoor gardens in Germany, plants flower from April to October; plants do not require a cooling treatment for flower initiation and development.

*Flower longevity*.—Flowers last about two weeks on the plant; flowers not persistent.

*Umbel height*.—About 6.5 cm.

*Umbel diameter*.—About 8 cm.

*Flower diameter*.—About 4.5 cm.

*Flower depth (height)*.—About 3 cm.

*Flower buds*.—Length: About 1.5 cm. Diameter: About 5 mm. Shape: Spindle-shaped. Color: Close to 146B.

*Petals*.—Quantity per flower: Five or six arranged in a single whorl; petals imbricate. Length, upper petals: About 3.7 cm. Length, lower petals: About 3.3 cm. Width, upper petals: About 2.4 cm. Width, lower petals: About 2 cm. Shape, all petals: Obovate; undulate. Apex, all petals: Rounded. Base, all petals: Cuneate. Margin, all petals: Entire. Texture, all petals, upper and lower surfaces: Smooth, glabrous; velvety. Color, all petals: When opening and fully opened, upper surface: Close to 46B and 62A; venation, close to 64A; colors becoming closer to 46B and 62B with development. When opening and fully opened, lower surface: Close to 56D; venation, close to 64A.

*Sepals*.—Quantity per flower: Five, arranged in a single whorl. Length: About 1.5 cm. Width: About 3 mm to 4 mm. Shape: Lanceolate. Apex: Acute. Margin: Entire. Texture, upper and lower surfaces: Pubescent. Color, upper and lower surfaces: Close to 144A.

*Peduncle (umbel stem)*.—Length: About 4.5 cm. Diameter: About 2 mm. Strength: Strong, flexible. Angle: Slightly outwardly slanted. Texture: Moderately pubescent. Color: Close to 146B.

*Pedicel (individual flower stem)*.—Length: About 2.5 cm. Diameter: About 1 mm. Strength: Strong; flexible. Angle: Slightly outwardly slanted. Texture: Moderately pubescent. Color: Close to 146B.

*Reproductive organs*.—Androecium: Stamen quantity per flower: About ten. Anther length: About 2 mm. Anther shape: Tubular. Anther color: Close to 79A. Pollen amount: Abundant. Pollen color: Close to 167A. Gynoecium: Pistil quantity per flower: One. Pistil length: About 1.7 cm. Stigma shape: Five to six-parted. Stigma color: Close to 59A. Style length: About 1 cm. Style color: Close to 59C. Ovary color: Close to 147C. Seeds and fruits: Seed and fruit development have not been observed on plants of the new Regal Geranium.

Disease & pest resistance: Plants of the new Regal Geranium have not been observed to be resistant to pathogens and pests common to Regal Geranium plants.

Temperature tolerance: Plants of the new Regal Geranium have been observed to tolerate temperatures ranging from about 1° C. to about 35° C. to 40° C.

It is claimed:

1. A new and distinct Regal Geranium plant named 'Campeacl' as illustrated and described.

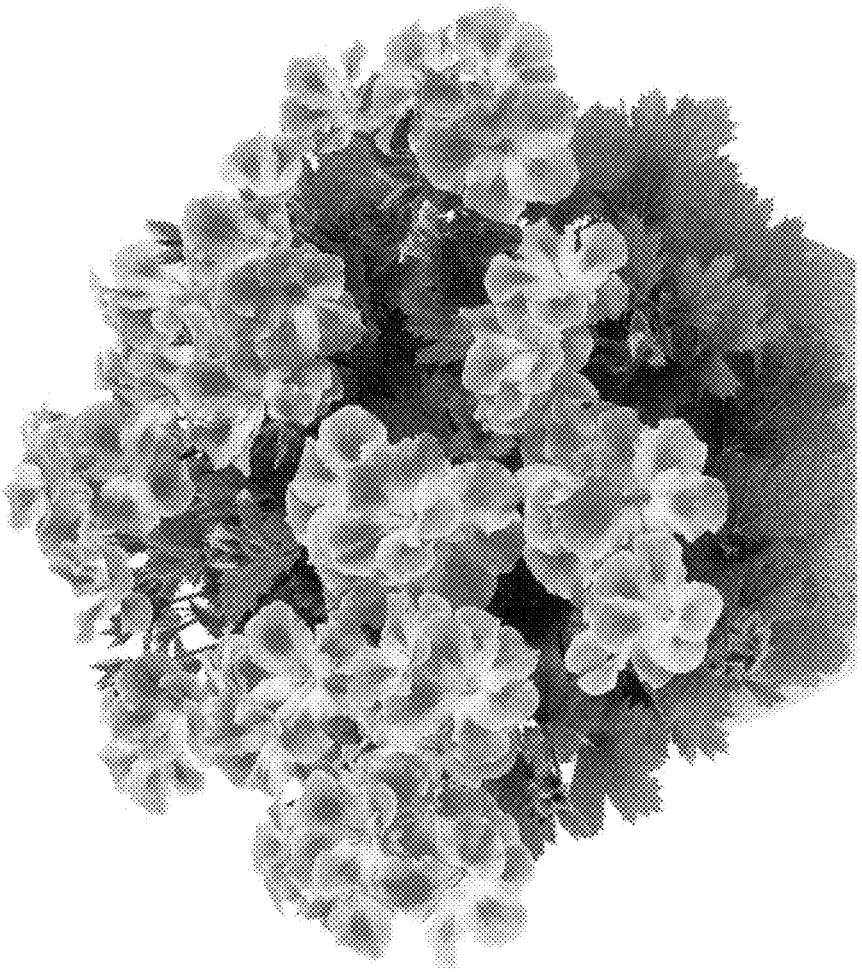

* * * * *